United States Patent [19]

Kato et al.

[11] Patent Number: 4,798,886
[45] Date of Patent: Jan. 17, 1989

[54] MUTUAL SEPARATION OF PROTEINS

[75] Inventors: Koichi Kato, Kawabe; Takao Yamada, Matsubara; Kenji Kawahara, Izumi, all of Japan

[73] Assignee: Takeda Chemical Industries, Ltd., Osaka, Japan

[21] Appl. No.: 25,269

[22] Filed: Mar. 12, 1987

[30] Foreign Application Priority Data

Mar. 24, 1986 [JP] Japan ................................ 61-066399

[51] Int. Cl.[4] ............................................. C07K 3/18
[52] U.S. Cl. ................................... 530/416; 530/412; 530/417; 530/350; 530/351; 435/68; 435/183
[58] Field of Search ............... 530/351, 416, 417, 412; 435/68

[56] References Cited

U.S. PATENT DOCUMENTS 4,736,020 4/1988 Hillen .

FOREIGN PATENT DOCUMENTS 8505631 12/1985 World Int. Prop. O. .
8602068 4/1986 World Int. Prop. O. .

OTHER PUBLICATIONS

Kato et al., *Biochem. Biophys. Res. Com.* 1985, vol. 130, pp. 692–699.
Kato et al., EA vol. 105, 1986, #222217b.
Protein Purification, ed Scopes, 1982, pp. 138–139.
Yamaha et al. CA vol. 104, 1986, #205032z.
Moriya et al., CA vol. 105, #207347a.
Yamada et al., *Biochem. Biophys. Res. Comm.*, 135: 837–843 (Mar. 28, 1986).
Moriya et al., *Bio/Technology*, 4: 904–905 (Oct. 1986).
Kawasaki et al., *Eur. J. Biochem.* 152: 361–371 (1985).
Bernardi, "Chromatography of Proteins on Hydroxyapatite", *Methods in Enzymology* 27: 471–479 (1973).
Bernardi; "Chromatography of Proteins on Hydroxyapatite", *Methods in Enzymology*, vol. 22, pp. 325–339 (1971).

*Primary Examiner*—John Kight
*Assistant Examiner*—Garnette D. Draper
*Attorney, Agent, or Firm*—David G. Conlin; Stephan P. Williams

[57] ABSTRACT

A protein and a derivative thereof having a methionine residue added at the amino terminus are mutually separated with the utilization of the difference in affinity for hydroxyapatite between them, such as by means of liquid chromatography using a hydroxyapatite column.

17 Claims, 1 Drawing Sheet

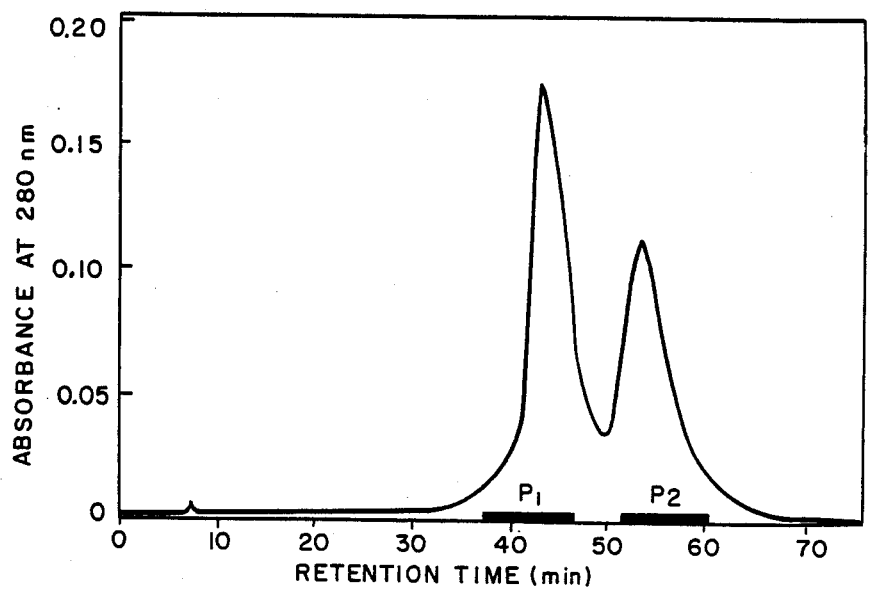

```
                              1
            X-Ala Pro Thr Ser Ser Ser Thr Lys Lys Thr Gln Leu Gln
                                            20
            Leu Glu His Leu Leu Leu Asp Leu Gln Met Ile Leu Asn

Gly Ile Asn Asn Tyr Lys Asn Pro Lys Leu Thr Arg Met
             40
            Leu Thr Phe Lys Phe Tyr Met Pro Lys Lys Ala Thr Glu
                                            60
            Leu Lys His Leu Gln Cys Leu Glu Glu Glu Leu Lys Pro

Leu Glu Glu Val Leu Asn Leu Ala Gln Ser Lys Asn Phe
                 80
            His Leu Arg Pro Arg Asp Leu Ile Ser Asn Ile Asn Val
                                           100
            Ile Val Leu Glu Leu Lys Gly Ser Glu Thr Thr Phe Met

Cys Glu Tyr Ala Asp Glu Thr Ala Thr Ile Val Glu Phe
                120
            Leu Asn Arg Trp Ile Thr Phe Cys Gln Ser Ile Ile Ser
                133
            Thr Leu Thr
```

FIG. 1

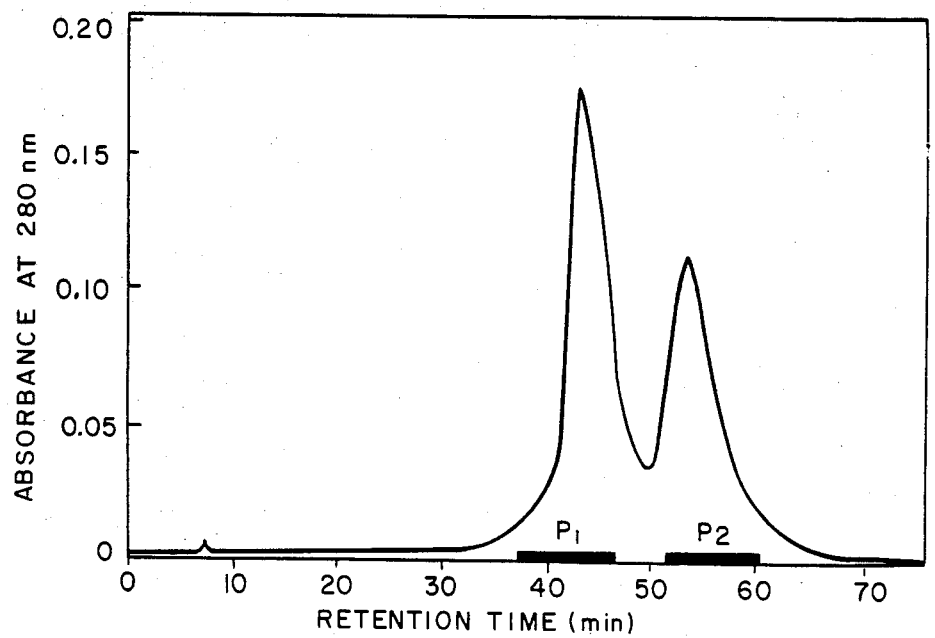

FIG. 2

MUTUAL SEPARATION OF PROTEINS

BACKGROUND OF THE INVENTION

This invention relates to a method of mutually separating proteins.

There has been revealed the existence of a variety of biologically active proteins such as cytokines and peptide hormones. Recent progress of genetic engineering techniques is leading to the mass-production of such biologically active proteins and application thereof for clinical use.

These proteins, which are produced using genetic engineering techniques, often pose a problem of the necessity for separation of the end product from other substances especially when the product produced by the expression of the gene coding for the desired protein is a mixture of the desired protein and a second protein which has a methionine residue added to the amino terminus of the desired protein. The additional methionine is derived from the expression of the translational initiation codon ATG which instructs to initiate the expression of the desired gene and failure of the expression system of the host cells to remove the added methionine from the expression product. This problem is encountered both in prokaryotic and eukaryotic hosts, but more often caused in the expression of genes in prokaryotic hosts.

When both a desired protein and its N-Met derivative are produced as a mixture, it is extremely difficult to mutually separate the two proteins because the difference in physicochemical properties therebetween, if any, is very small.

The methionine residue has a molecular weight of about 131 and is moderately hydrophobic and electrically neutral because of the absence of a dissociating group. Therefore, the presence or absence of one methionine residue at the amino terminus of a macromolecule, such as a protein, having a number of dissociating groups, hydrophobic groups and hydrophilic groups, is considered to have almost no influence on the physicochemical properties of the macromolecule. Thus, it is extremely difficult to mutually separate one molecular species having a methionine residue at the amino terminus from another having no such a methionine residue.

This difficult problem is involved in a great number of proteins and becomes especially severe when *Escherichia coli* is used as an expression host.

There is a possibility that a protein with a methionine residue at the amino terminus differs from a protein without such a methionine residue in their higher structures, and biological activities or biological stability in vivo and in vitro. There is also a possibility that the addition of a methionine residue to the amino terminus of a protein alters the antigenicity thereof. Therefore, it is desired, from the standpoint of physiology and industrial utilization, to establish a technique for separating a protein having a methionine residue at the amino terminus from another having no such methionine residue and to isolate each protein in a substantially pure form.

SUMMARY OF THE INVENTION

The present inventors have made an extensive study with a view toward developing a method of mutually separating a protein and its derivative which has a methionine residue added at the amino terminus of the protein (N-Met protein). As a result, it has been unexpectedly found that they have different adsorptivity to hydroxyapatite from each other. The present invention has been made on the basis of the new finding.

The present invention provides a method of mutually separating a protein or a Met-protein from a mixture comprising the protein and Met-protein, which comprises subjecting the mixture to a separation procedure utilizing the difference in the affinity for hydroxyapatite between the protein and the Met-protein.

It is, therefore, an object of the present invention to provide an effective method for separating a protein, especially interleukin-2, from a derivative thereof having a methionine added at the amino terminus thereof. The thus obtained protein and Met-protein are useful as drugs.

BRIEF DESCRIPTION OF THE DRAWINGS

Other objects, features and advantages of the present invention will become apparent from the detailed description of the invention which follows, when considered in light of the accompanying drawings, in which:

FIG. 1 is the amino acid sequence of IL-2 (X=hydrogen) and Met-IL-2 (X=methionine); and FIG. 2 is an elution pattern in high performance liquid chromatography of Example 1 described hereinafter.

DETAILED DESCRIPTION OF THE INVENTION

The term "protein" used in the present specification is intended to refer to a high molecular weight substance which has a primary structure consitituted from amino acids and which includes those with and without glycoside chains, and polypeptides chemically or structurally modified by, for example, chemical or enzymatic reactions.

The term "Met-protein" used in the present specification is intended to refer to a derivative of the above "protein" having an additional methionine residue at the amino terminus. The present invention is especially concerned with mutual separation of a desired protein and its Met-protein which has the same or almost the same biological activity as the desired protein. The Met-protein in the present invention preferably has such a sufficient similarity to the protein in the amino acid sequence as to exhibit the biological activity of the desired protein.

The term "biological activity" as used in the present specification is intended to refer to an activity or effect, inclusive of physiological or immunological activity and effect, on organisms and/or physiological substances including cells which may be or may not be living in vivo or in vitro, portions of the cells, products based on the physiological functions of the cells, etc., an biological substances.

Such a mixture of a protein and a derivative thereof having a methionine residue added thereto (Met-protein) may be generally produced by genetic engineering techniques and, generally, by expression of the recombinant gene using as a host strains belonging to the genus Escherichia or the genus Bacillus, yeasts or animal cells.

Such proteins may be various biologically active proteins including, for example, cytokine such as interleukins (interleukin-1, interleukin-2, etc.), B cell growth factor (BGF), B cell differentiation factor (BDF), macrophage activating factor (MAF), lymphotoxin (LT) and tumor necrosis factor (TNF); transforming growth factor (TGF-α); peptide and protein hormones such as erythropoietin, epithelium cell growth factor, insulin and human growth hormones; antigenic proteins of pathogenic microorganisms such as hepatitis B virus antigen, influenza antigen, aphtha virus antigen and plasmodium antigen; enzymes such as peptidases (e.g. tissue plasminogen activator, urokinase, serrapeptase) and lysozyme; and a plasma proteins such as human serum albumin (HSA).

The method of the present invention is advantageously applied to the separation of proteins having a molecular weight of about 3,000 to 50,000, especially about 5,000 to 30,000, or having the number of amino acids of about 30 to 500, especially about 50 to 300.

Interleukin-2 is an especially preferred example of such a protein.

Any interleukin-2 may be used for the purpose of the present invention as long as it has the same biological or immunological activity, such as capability of binding with interleukin-2 receptor or anti-interleukin-2 antibody, as natural human interleukin-2. Illustrative of suitable interleukin-2 proteins are a polypeptide (I) having the amino acid sequence shown in FIG. 1 (in which X represents hydrogen) and fragments of the polypeptide (I) containing an amino acid sequence necessary for exhibiting biological or immunological activity. Examples of such fragments include a fragment having one amino acid deleted from the amino terminus of the polypeptide (I) [European Publication No. 91539], a fragment having four amino acids deleted from the amino terminus of the polypeptide (I) [Unexamined Japanese Patent Publication No. 60-126088], fragments having several amino acids deleted from the carboxyl terminus of the polypeptide (I). The polypeptide (I) in which a portion of the amino acids is deleted or substituted with other amino acid(s) may also be used. A polypeptide in which cysteine at the 125th amino acid of the polypeptide (I) is substituted with serine [Japanese Unexamined Patent Publication No. 59-93093, U.S. Pat. No. 4,518,584 or European Publication No. 109748] is one such example. The polypeptides are preferred not to be glycosylated. Interleukin-2 having the amino acid sequence shown in FIG. 1 is especially preferred.

In the present specification, the polypeptide having the amino acid sequence which is shown in FIG. 1 and in which X is hydrogen is hereinafter referred to as "IL-2" for brevity and the polypeptide of FIG. 1 in which X is methionine is referred to as "Met-IL-2".

The ratio of the above protein and Met-protein in the mixture is not specifically limited. The mixture preferably has a purity of at least about 50%, more preferably at least about 80%.

Hydroxyapatite to be used in the method of the present invention is a kind of calcium phosphate and may be expressed by the formumla: $Ca_{10}(PO_4)_6(OH)_2$.

Hydroxyapatite for use in chromatography or high performance liquid chromatography may be suitably utilized in the method of the present invention. As hydroxyapatite for chromatography, there may be mentioned Biogel HT, Biogel HTP (both manufactured by Biorad Inc., U.S.A.), Hydroxy-apatite (manufactured by Nippon Chemical K.K. Japan) etc. The high performance liquid chromatography column may be, for example, Hydroxyapatite column (manufactured by Mitsui Toatsu K.K. Japan), Biogel HPHT Column (manufactured by Biorad Inc.), KB column (manufactured by Koken K.K. Japan) etc.

The separation treatment adopted in the present invention may be, for example, conventional chromatography or high performance liquid chromatography.

The chromatography may be performed by applying proteins to be separated to a hydroxyapatite column previously equilibrated with an initiation buffer and, then, by eluting the proteins with an elution buffer for separation. As the initiation buffer, a phosphate buffer having a pH of at least about 5, more generally a phosphate buffer (pH of about 6.8) of 0.01 M or lower may be used. The amount of the protein sample to be applied to the column is suitably about 1 to 5 mg per 1 ml of hydroxyapatite. As the elution buffer, a high concentration phosphate buffer having the same pH as the initiation buffer is generally used, though the elution may be effected with the use of an acetate, oxalate, carbonate or sulfate buffer. Both stepwise and linear gradients elution may be adopted.

The high performance liquid chromatography may be conducted under almost the same conditions as the above-described conventional chromatography. In particular, 0.01 M sodium phosphate buffer having a pH of about 5.5 to 10.5, preferably about 6.5 to 8 is used as an equilibration buffer and a sodium phosphate buffer with an increased concentration is used for elution, when the high performance liquid chromatography is effected with the use of, for example, a commercially available Hydroxyapatite column (0.78×10 cm, manufactured by Mitsui Toatsu K. K.). Generally, about 0.1 to 100 mg of a protein sample is applied on the colum and the high performance liquid chromatography is performed at an elution rate of about 0.1 to 5 ml/min, more preferably about 0.5 to 1.5 ml/min.

The fractions which are obtained by the above separation treatment and which respectively contain the protein and the Met-protein allow the protein and the Met-protein to be obtained separately in substantially pure form. For this purpose, a suitable combination of conventional protein purification techniques such as dialysis, hydrophobic chromatography, gel filtration, ion exchange chromatography and high performance liquid chromatography may be adopted.

The present invention is effective in separating a protein produced by genetic engineering techniques from its corresponding Met-protein to the extent that the separated protein is substantially free from the Met-protein. More particularly, the content of the Met-protein in the protein product or the content of the protein in the Met-protein product obtained in accordance with the method of the present invention is 3% by weight or less, preferably 2% or less, especially 1% or less.

The protein and the derivative thereof having methionine added to the protein (Met-protein) have the same biological or immunological activity as their corresponding natural proteins and are highly purified and free of other proteins as impurities or pyrogenic substances so that they may be safely used for injection preparations.

For instance, IL-2 and Met-IL-2 obtained by the method according to the present invention have an activity to permit the growth of the normal T cells and natural killer cells with their functions being maintained in normal state. Therefore, IL-2 and Met-IL-2 obtained by the method of the present invention may be utilized for in vitro propagation of T cells or natural killer cells for generations over a long period of time, or cloning of the cells. This property permits measurement of the activity of IL-2 and Met-IL-2.

Further, IL-2 and Met-IL-2 permit the selective growth, in vitro, of antigen-specific killer T cells which recognize tumor antigens and destroy the same and of natural killer cells which are capable of killing tumor cells irrespective of experience or inexperience of antigen sensitization. The anti-tumor effect of the killer T cells may be improved by inoculating IL-2 or Met-IL-2 simultaneously at the incorporation of the T cells into an organism. Accordingly, IL-2 and Met-IL-2 obtained according to the present invention may be used for the prevention and therapy of tumors and the therapy of immune dysfunction of warm blooded mammals (e.g. mouse, rat, rabbit, dog, cat, pig, horse, sheep, ox, human).

IL-2 and Met-IL-2 obtained by the method of the present invention are free of antigenic impure proteins and are low in toxicity.

When IL-2 or Met-IL-2 is used as an agent for the prevention or therepy of tumors, the protein is mixed and diluted with suitable known carrier, excipient and/or diluent so as to be suited for parenteral or oral dosage in the form of injection, capsules or the like. As mentioned previously, IL-2 and Met-IL-2 may be used alone or in combination with killer T cells or natural killer cells which have been grown in vitro.

IL-2 and Met-IL-2 obtained in the present invention have substantially the same biological activity as known isolated natural human interleukin-2 and, thus, can be used in the same manner as the natural one. Because of the extremely small dissociation constant between IL-2 or Met-IL-2 and interleukin-2 receptors, the dosage of IL-2 or Met-IL-2 may be very small.

When used for the purpose of propagating T cells in vitro, IL-2 or Met-IL-2 may be added to a medium in a concentration of about 0.01 to 1 unit/ml, preferably 0.1 to 0.5 unit/ml.

The biological activity of interleukin-2 may be measured by a method disclosed in Biochemical and Biophysical Research Communications 109, 363 (1982) using interleukin-2 dependent cells.

One example of the use of IL-2 or Met-IL-2 for the in vitro propagation of T cells is a method which includes adding both T cells ($1 \times 10^6$/ml) separated from human peripheral blood and B cell transformant ($1 \times 10^6$/ml) irradiated with X-ray (1500 rad) to an RPMI 1640 medium containing 20% bovine fetal serum, maintaining the mixture at 37° C. for 3 days in the presence of 5% of $CO_2$ in lymphocyte mixing cultivation, thereby to obtain a cell suspension liquid containing T cells sensitized with alloantigen, adding IL-2 or Met-IL-2 to the suspended liquid in a concentration of 0.1 to 0.5 unit/ml, and continuing the culture of the resulting mixture for about 1 month while replacing the culture medium with the fresh medium once a week.

The abbreviations of amino acids used in the present specification and in FIG. 1 are in accordance with IUPAC-IUB Commission on Biochemical Nomenclature or customarily used nomenclature. Examples of such abbreviations are as shown below, in which the configuration of the amino acids having optical isomers is L-form except otherwise specifically noted.

Gly: Glycine
Ala: Alanine
Val: Valine
Leu: Leucine
Ile: Isoleucine
Ser: Serine
Thr: Threonine
Cys: Cysteine
½Cys: Half cystine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
Asp/Asn: Aspartic acid and Asparagine
Glu/Gln: Glutamic acid and Glutamine The following examples will further illustrate the present invention but should not be construed as limiting te present invention thereto. The measurement of the biological activity is in accordance with a method using interleukin-2 dependent cells [Biochem. Biophys. Res. Comn. 109, 363 (1982)].

EXAMPLE 1

Separation of IL-2 and Met-IL-2 by High Performance Liquid Chromatography Using Hydroxyapatite Column To a hydroxyapatite column (0.78×10 cm, 4.8 ml, manufactured by Mitsui Toatsu K.K., Japan) for high performance liquid chromatography was applied 2 ml (2.06 mg protein) of 0.005 M ammonium acetate buffer (pH 5.0) (protein concentration:1.03 mg/ml) containing non-glycosylated human interleukin-2 which was obtained in hereinafter described Reference Example 1 and which was a mixture of IL-2 and Met-IL-2, and the protein was eluted under the following conditions:

Column temperature: 25° C.
Elution solvent A: 0.01M sodium phosphate buffer (pH 7.5)
Elution solvent B: 0.25M sodium phosphate buffer (pH 7.5)
Elution program: 0 min (95% A+5% B)—45 min (87% A+13% B)—65 min (87% A+13% B)
Elution rate: 0.6 ml/min
Wavelength monitored: 280 nm As a result, the non-glycosylated interleukin-2 was separately eluted as the first peak at a retention time of 43 min and the second peak at a retention time of 54 min. The two fractions were each recovered and, in order to remove sodium phosphate used in the chromatography, subjected to high performance liquid chromatography using a trifluoroacetic acid-acetonitrile elution solvent under the following conditions:

Column: Ultrapore RPSC (1.0×25 cm, manufactured by Altex Inc., U.S.A.)
Column temperature: 30° C.
Elution solvent A: 0.1% trifluoroacetic acid-99.9% water
Elution solvent B: 0.1% trifluoroacetic acid-99.9% acetonitrile
Elution program: 0 min(55% A+45% B)—4 min (55% A+45% B)—28 min (42% A+58% B)—38 min (34% A+66% B)—43 min (20% A+80% B)—44 min (55% A+45% B)
Elution rate: 3.0 ml/min The active fractions were pooled and lyophilized to obtain white powder. The powder products from the first and second peaks in the hydroxyapatite column chromatography were named P1 and P2, respectively. The yields of P1 and P2 were 0.80 mg (38.8%) and 0.46 mg (22.3%), respectively.

The protein products P1 and P2 [each 45 μg (3 nmol)-]were chemically analyzed for the determination of their N-terminal amino acid sequences by means of automated Edman degradation method using a gas phase protein sequencer (Type 470A manufactured by Applied Biosystems Inc.). The phenylthiohydantoin-amino acid (PTH-amino acids) produced at each cycle was identified by high performance liquid chromatography using Micropack SP-C18 column (manufactured by Varian Inc.). The PTH-amino acids detected in cycle 1 through 4 are shown in Table 1.

TABLE 1

| Cycle | PTH-amino acid detected (pmol) | | | |
|---|---|---|---|---|
| | P 1 | | P 2 | |
| 1 | Ala (62) | Met (2450) | Ala (2010) | Met (106) |
| 2 | Pro (38) | Ala (2370) | Pro (1690) | Ala (68) |
| 3 | Thr (45) | Pro (1880) | Thr (1070) | Pro (57) |
| 4 | Ser (18) | Thr (1210) | Ser (455) | Thr (31) |

The amino acid at the carboxyl terminus of each protein, P1 and P2, was analyzed as follows: P1 and P2, respectively was sampled into a glass tube, to which was then added anhydrous hydrazine. After sealing the glass tube in vacuo, the mixture in the glass tube was reacted at 100° C. for 6 hours. The resulting hydrazine-decomposed mixture was then treated with benzaldehyde and was subjected to amino acid analysis using model 835 amino acid analyzer (manufactured by Hitachi Ltd.) for measurement of the liberated amino acid. Threonine only was detected in both of the proteins P1 and P2, with a recovery of 30.3% and 28.5%, respectively. Thus, P1 and P2 were determined to have threonine at their carboxyl terminus.

Amino acid analyses of P1 and P2 were carried out by a method including charging the sample into glass tubes together with constant boiling point hydrochloric acid containing 4% thioglycolic acid, sealing the tubes in vacuo, heating the mixture within the tubes at 110° C. for 24, 48 and 72 hours, and analyzing each of the hydrolyzed mixtures by means of an amino acid analyzer (model 835, manufactured by Hitachi Ltd., Japan). The analysis of cysteine and cystine was carried out by oxidizing the sample with performic acid, hydrolyzing the oxidized mixture with constant boiling point hydrochloric acid for 24 hours in vacuo and applying the hydrolyzed mixture on the amino acid analyzer for quantitatively analyzing cysteic acid. Analytic values were each calculated as an average of the results of 24, 48 and 72 hour hydrolysis. The analytical values of serine and threonine were obtained by the extrapolation to zero hour hydrolysis. The results are shown in Table 2. The results of the analysis of N-terminal amino acid sequence and the amino acid composition reveal that P1 contains Met-IL-2 (the protein shown in FIG. 1 in which X is methionine) with a purity of 97% or more and that P2contains IL-2 (the protein shown in FIG. 1 in which X is hydrogen) with a purity of 95% or more.

TABLE 2

| | Number of residues per molecule | | |
|---|---|---|---|
| Amino acid | P1 | P2 | Values predicted from cDNA sequence |
| Asp/Asa | 11.9 | 12.0 | 12 |
| Thr | 12.6 | 12.8 | 13 |
| Ser | 7.5 | 7.6 | 8 |
| Glu/Gln | 18.6 | 18.8 | 18 |
| Pro | 5.0 | 4.9 | 5 |
| Gly | 2.4 | 2.2 | 2 |
| Ala | 5.2 | 5.0 | 5 |
| ½ Cys | 2.7 | 2.7 | 3 |
| Val | 3.9 | 3.9 | 4 |
| Met | 4.9 | 4.0 | 4 |
| Ile | 8.2 | 8.3 | 9 |
| Leu | 21.9 | 22.4 | 22 |
| Tyr | 3.3 | 3.3 | 3 |
| Phe | 6.0 | 6.2 | 6 |
| Lys | 10.9 | 10.9 | 11 |
| His | 3.0 | 3.0 | 3 |
| Arg | 4.1 | 4.0 | 4 |
| Trp | 1.0 | 1.1 | 1 |

REFERENCE EXAMPLE 1

Preparation of Non-Glycosylated Human Interleukin-2

(i) Construction of Expression Plasmid:

Plasmid pILOT 135-8 (Japanese Unexamined Patent Publication No. 60-115528 or European Patent Publication No. 145390) bearing the human interleukin-2 gene was cleaved with restriction enzyme HgiAI. Thus obtained DNA fragment of 1294bp was treated with T4 DNA polymerase to form a blunt end to which was linked an EcoRI linker dTGCCATGAATTCATG-GCA using T4 DNA ligase. The resulting DNA was digested with EcoRI to obtain a DNA fragment bearing a translational initiation codon ATG and the human interleukin-2 gene.

The DNA fragment thus obtained was inserted, with T4 DNA ligase, into ptrp 781 [Nucleic Acids Research 11, 3077 (1983)]at EcoRI-PstI sites which was previously digested. Thus obtained expression plasmid pTF1 contained the translational initiation codon and human interleukin-2 gene in the downstream of its trp promoter.

The plasmid pTF1 was cleaved with restriction enzyme StuI and linked with BamHI linker. The resulting plasmid DNA was then treated with restriction enzymes BamHI and EcoRI and was inserted into the EcoRI-BamHI sites of plasmid pTB281 having λpL promoter, thereby to obtain expression plasmid pTB285.

(ii) Production of Transformant:

Escherichia coli N4830 was transformed with plasmid pTB285 according to the method of Cohen et al [Proc. Natl. Acad. Sci. USA 69, 2110 (1972)]to obtain transformant Escherichia coli N4830/pTB285 bearing the above plasmid pTB285.

The transformant Escherichia coli N4830/pTB285 has been deposited at Institute for Fermentation, Osaka (IFO), Japan under the accession number of IFO 14437 since Apr. 25, 1985. And the transformant has been also deposited with Fermentation Research Institute, Agency of Industrial Science and Technology, Ministry of International Trade and Industry (FRI), Japan under the accession number of FERM P-8199 since Apr. 30, 1985, and the deposit has been changed to the deposit according to Budapest Treaty and the transformant has been stored at FRI under the accession number of FERM BP-852.

(iii) Cultivation of Transformant:

Transformant *Escherichia coli* N4830/pTB285 (IFO 14437, FERM BP-852) was seeded in a 250 ml flask containing 50 ml of a medium (pH 7.0) which contained 1% Bacto tripton (Difco Laboratory, USA), 0.5% Bacto yeast extract (Difco Laboratory, USA), 0.5% NaCl and 50 μg/ml ampicillin and incubated at 37° C. overnight with shaking. The culture liquid was transferred to a 5 liter jar fermenter containing 2.5 liters of M9 medium containing 0.5% Casamino acid, 0.5% glucose and 50 μg/ml ampicillin and cultivated at 35° C. for 6 hours and then at 42° C. for 3 hours with aeration agitation. The culture was then centrifuged to collect cells and the cells were frozen at −80° C. for storage.

(iv) Extraction:

The frozen cells (20 g) were homogeneously suspended in 100 ml of an extraction buffer (pH 7.0) containing 7M quanidine hydrochloride and 0.1 M Tris-HCl and the suspension was stirred at 4° C. for 1 hour, followed by centrifugation at 28,000xg for 20 min, thereby to obtain a supernatant.

(v) Partial Purification of Interleukin-2 Protein:

The supernatant was dialyzed against 0.01 M Tris-HCl buffer (pH 8.5) and then centrifuged at 19,000xg for 10 min. The resulting supernatant was applied to 50 ml DE52 column (DEAE-cullulose, manufactured by Wattman Inc., UK) previously equilibrated with 0.01 M Tris-HCl buffer (pH 8.5), to adsorb the protein. Elution of interleukin-2 was performed with a NaCl linear gradient elution (0–0.15 M NaCl, 1 liter) to collect the active fraction.

(vi) Purification of Interleukin-2 Protein:

The active fraction obtained above was concentrated to 5 ml using YM-5 membrane (manufactured by Amicon Inc., USA) and the concentrate was subjected to a gel filtration using 500 ml Sephacryl S-200 column (manufactured by Pharmacia, Sweden) previously equilibrated with 0.1 M Tris-HCl (pH 8.0)-1 M NaCl buffer. The active fraction thus obtained (40 ml) was then concentrated to 3 ml using YM-5 membrane. The concentrate was applied on Ultrapore RPSC column (manufactured by Altex Inc., USA) to be adsorbed and high performance liquid chromatography was conducted under the following conditions using trifluoroacetic acid-acetonitrile buffer as an elution solvent:

Column: Ultrapore RPSC (4.6x 75mm)
Column Temperature: 30° C.
Elution solvent A: 0.1% trifluoroacetic acid-99.9% water
Elution solvent B: 0.1% trifluoroacetic acid-99.9% acetonitrile
Elution program: 0 min (68% A +32% B)—25 min (55% A +45% B)—35 min (45% A +55% B)—45 min (30% A +70% B)—48 min (100% B)
Elution rate: 0.8 ml/min
Wavelength monitored: 230 nm Active fraction (10 ml) eluted at a retention time of about 39 min which comprises a mixture of IL-2 and Met-IL-2 was obtained.

The following references, which are referred to for their disclosures at various points in this application, are incorporated herein by reference.

European Patent Publication No. 91539
Japanese Unexamined Patent Publication No. 60-126088
Japanese Unexamined Patent Publication No. 59-93093
U.S. Pat. No. 4,518,584
European Patent Publication No. 109748
Biochem. Biophys. Res. Comn. 109, 363 (1982)
Japanese Unexamined Patent Publication No. 60-115528
European Patent Publication No. 145390
Nucleic Acids Research 11, 3077 (1983)
Proc. Natl. Acad. Sci. USA 69, 2110 (1972)

What is claimed is:

1. A method of mutually separating a protein or a Met-protein from a mixture comprising the protein and Met-protein, which comprises subjecting the mixture to a separation procedure utilizing the difference in the affinity for hydroxyapatite between the protein and the Met-protein.

2. A method according to claim 1, wherein the separation procedure comprises subjecting the mixture to chromatography using a hydroxyapatite column.

3. A method according to claim 2, wherein the chromatography is high performance liquid chromatography.

4. A method according to claim 1, wherein the mixture comprising the protein and the Met-protein is produced by a genetic engineering technique.

5. A method according to claim 1, wherein the protein is a cytokine, transforming growth factor, a peptide and protein hormone, an antigenic protein of a pathogenic microorganism, an enzyme or a hemoprotein.

6. A method according to claim 1, wherein the protein has a molecular weight of about 3,000 to 50,000.

7. A method according to claim 6, wherein the molecular weight is 5,000 to 30,000.

8. A method according to claim 1, wherein the protein comprises about 30 to 500 amino acids.

9. A method according to claim 8, wherein the protein comprises 50 to 300 amino acids.

10. A method according to claim 1, wherein the protein and the Met-protein are non-glycosylated.

11. A method according to claim 1, wherein the protein is a cytokine.

12. A method according to claim 11, wherein the cytokine is an interleukin-2.

13. A method according to claim 12, wherein the interleukin-2 is a non-glycosylated protein having the amino acid sequence shown in the following sequence where X is hydrogen:

1
X—Ala Pro Thr Ser Ser Ser Thr Lys Lys Thr Gln Leu Gln

20
Leu Glu His Leu Leu Leu Asp Leu Gln Met Ile Leu Asn

Gly Ile Asn Asn Tyr Lys Asn Pro Lys Leu Thr Arg Met

40
Leu Thr Phe Lys Phe Tyr Met Pro Lys Lys Ala Thr Glu

60
Leu Lys His Leu Gln Cys Leu Glu Glu Glu Leu Lys Pro

Leu Glu Glu Val Leu Asn Leu Ala Gln Ser Lys Asn Phe

80
His Leu Arg Pro Arg Asp Leu Ile Ser Asn Ile Asn Val

100
Ile Val Leu Glu Leu Lys Gly Ser Glu Thr Thr Phe Met

Cys Glu Tyr Ala Asp Glu Thr Ala Thr Ile Val Glu Phe

120
Leu Asn Arg Trp Ile Thr Phe Cys Gln Ser Ile Ile Ser

133
Thr Leu Thr

14. A method according to claim 1, wherein the mixture is a mixture of the protein and the Met-protein having a purity of not less than about 50%.

15. A method according to claim 14, wherein the purity is not less than 80%.

16. A method according to claim 1, wherein a non-glycosylated interleukin-2 and a non-glycosylated methionyl interleukin-2 having the amino acid sequence of the interleukin-2 and bearing an additional methionine residue at the amino terminus are separated from each other by subjecting the mixture comprising the interleukin-2 and the methionyl interleukin-2 to chromatography using a hydroxyapatite column.

17. A method according to claim 16, wherein the non-glycosylated interleukin-2 comprises the amino acid sequence shown in the following sequence where X is hydrogen:

1
X—Ala Pro Thr Ser Ser Ser Thr Lys Lys Thr Gln Leu Gln
20
Leu Glu His Leu Leu Leu Asp Leu Gln Met Ile Leu Asn
Gly Ile Asn Asn Tyr Lys Asn Pro Lys Leu Thr Arg Met
40
Leu Thr Phe Lys Phe Tyr Met Pro Lys Lys Ala Thr Glu
60
Leu Lys His Leu Gln Cys Leu Glu Glu Glu Leu Lys Pro
Leu Glu Glu Val Leu Asn Leu Ala Gln Ser Lys Asn Phe
80
His Leu Arg Pro Arg Asp Leu Ile Ser Asn Ile Asn Val
100
Ile Val Leu Glu Leu Lys Gly Ser Glu Thr Thr Phe Met
Cys Glu Tyr Ala Asp Glu Thr Ala Thr Ile Val Glu Phe
120
Leu Asn Arg Trp Ile Thr Phe Cys Gln Ser Ile Ile Ser
133
Thr Leu Thr

* * * * *